United States Patent [19]

Benjamin et al.

[11] Patent Number: 4,559,035
[45] Date of Patent: Dec. 17, 1985

[54] COLLAPSIBLE WOUND SUCTION EVACUATOR

[75] Inventors: Thomas A. Benjamin, Newcomerstown; Dean A. Ransom, Dover, both of Ohio

[73] Assignee: Snyder Laboratories, Inc., Dover, Ohio

[21] Appl. No.: 535,501

[22] Filed: Sep. 26, 1983

[51] Int. Cl.⁴ .................... A61M 1/06; A61M 37/00
[52] U.S. Cl. ................................... 604/73; 604/133; 604/181
[58] Field of Search ............... 92/89, 94; 128/205.16; 267/73, 74, 153; 141/23-25, 65; 604/131-134, 604/73, 181

[56] References Cited

U.S. PATENT DOCUMENTS

| | | |
|---|---|---|
| 3,115,138 | 12/1963 | McElvenny et al. ............. 128/278 |
| 3,742,952 | 7/1973 | Magers et al. .................... 128/278 |
| 3,774,611 | 11/1973 | Tussey et al. .................... 128/278 |
| 3,779,243 | 12/1973 | Tussey et al. .................... 128/278 |
| 3,809,086 | 5/1974 | Schachet ......................... 128/278 |
| 4,014,337 | 3/1977 | Treace ............................. 128/278 |
| 4,141,361 | 2/1979 | Snyder ............................ 128/278 |
| 4,161,179 | 7/1979 | Abramson ....................... 604/134 |
| 4,278,089 | 7/1981 | Huck et al. ...................... 128/278 |
| 4,429,693 | 2/1984 | Blake et al. ..................... 604/133 |
| 4,460,354 | 7/1984 | Weilbacher et al. ............. 604/73 |

FOREIGN PATENT DOCUMENTS 0048164 3/1982 European Pat. Off. .

OTHER PUBLICATIONS

Literature, "Promote Wound Healing with Uniform Gentle Suction", Innovative Surgical Products Inc., Santa Ana, Calif. 92705.
Innovative Surgical Products, Inc. brochure—"ISP-VAC Reservoir for Closed Wound Suction"—Date: 9-80.

Primary Examiner—J. L. Kruter
Attorney, Agent, or Firm—Margaret L. Geringer

[57] ABSTRACT

A self-contained, independently operable closed wound suction evacuator which is comprised of a box-like internal body structure disposed within a fluid tight, flexible outer pouch. The pouch includes an inlet/outlet valve for providing communication between the interior of the pouch and the atmosphere of the interior of the pouch and a drainage tube. The box-like internal body structure is capable of being in an engaged position or in a disengaged position. In the disengaged position, the internal box-like structure can remain in a flat condition without causing the tensioning member to be stretched or activated. When ready for use, the internal structure can be manually expanded into its box-like structure. When fully expanded the internal structure will become engaged, hence engaging the tensioning member. Subsequent compression of the internal structure to its flat position stretches the tensioning member and activates the evacuator. Upon subsequent release of the compressive force, the tensioning member will cause the internal structure to expand back into its box-like shape, hence developing a vacuum within the evacuator to draw fluid through a drainage tube and into the evacuator. The flexible pouch expands as the internal body structure expands.

37 Claims, 28 Drawing Figures

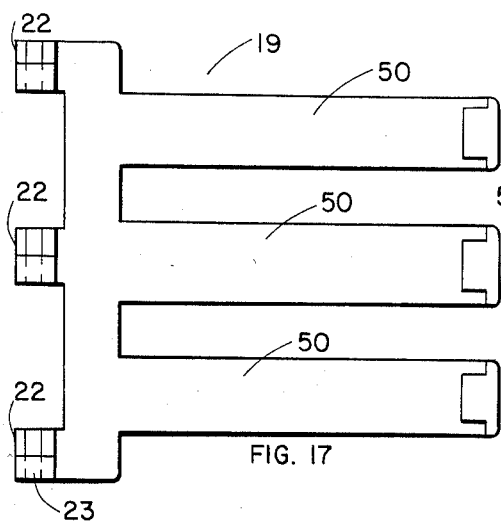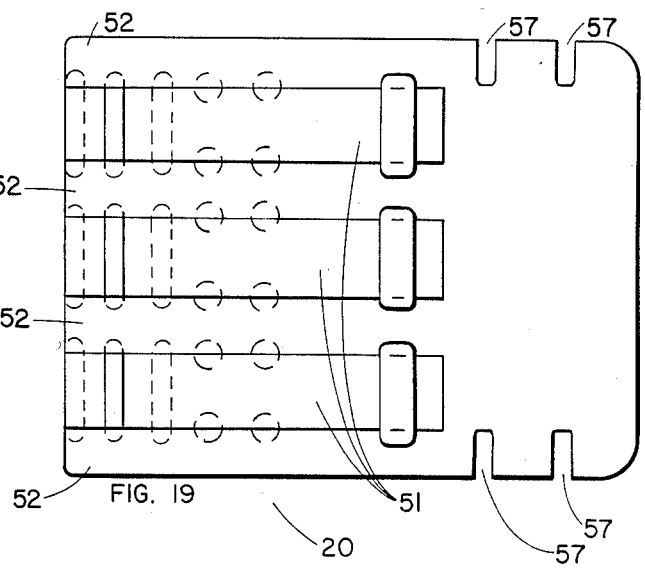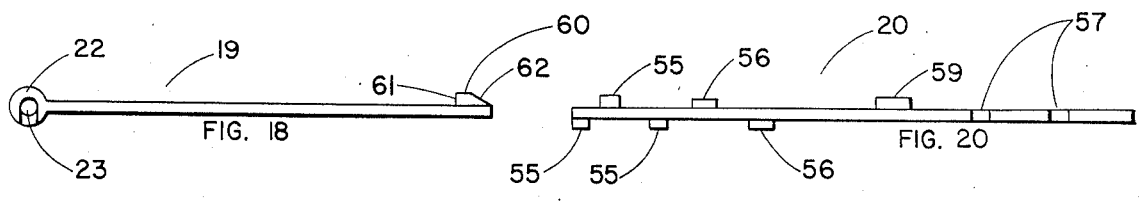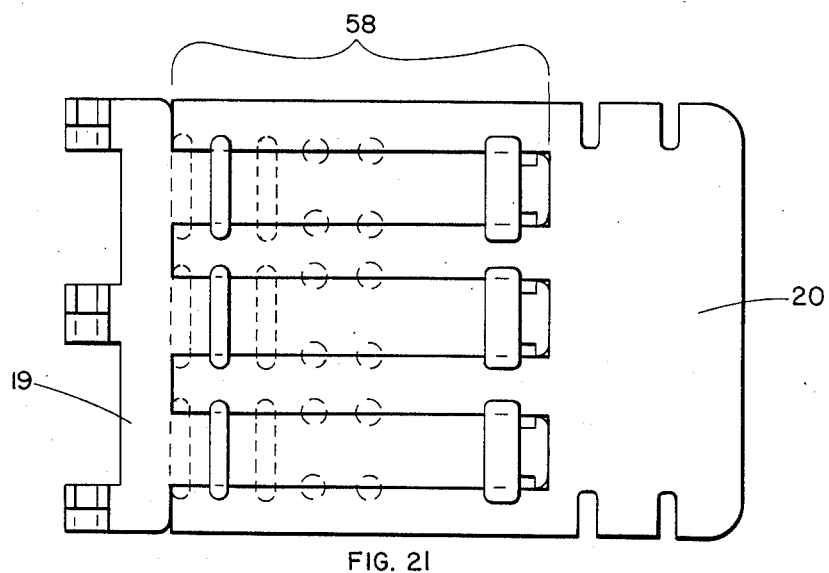

COLLAPSIBLE WOUND SUCTION EVACUATOR

BACKGROUND OF THE INVENTION

This invention relates to wound suction evacuators, and more particularly, to the type of wound suction evacuators that are self-contained and independently operable for the removal of fluid from the human body and the like.

In many surgical procedures, and occasionally as a result of traumatic injury, it is desirable to withdraw body fluids from the wound site to promote healing and prevent complications. Evacuator systems comprising a flexible container to create a vacuum have been used in the drainage of these fluids.

One such prior art container is described in U.S. Pat. No. 3,115,138 to McElvenney et al. The evacuator of the McElvenney et al patent utilizes a self-contained compressible fluid-tight container. In the McElvenney container, a plurality of springs are disposed between the top and bottom. The container and springs are compressed and subsequently released to permit expansion. The expansion of the sealed container develops a vacuum which can be applied through suitable wound drainage tubing connected to the container for the evacuation of fluids. The tubing is connected to the evacuator through a valve opening which provides communication between the interior of the evacuator and the drainage tubing. The other end of the suitable tubing is laid within the wound of a patient for post-operative drainage of the wound.

Other examples of prior art wound evacuator devices are described in the following U.S. Pat. Nos. 3,376,868; 3,742,952; 3,774,611; 3,779,243; 3,809,086; and 4,141,361.

Wound evacuators typically are sold in an expanded state which is bulky and cumbersome for shipping or storing. However, some devices are capable of being mechanically retained in their compressed state, although their resilient force exerting or tensioning member is typically activated when in such a compressed state. For example, European Patent Application EP No. 0 048 164 A to Blake, et al. includes a large spring disposed between its top and bottom surfaces. This evacuator is compressed, whereupon a mechanical means may be utilized to latch the evacuator in this position until ready for use. Therefore, this evacuator can be shipped in a flat position and remain in this position until ready for use. But this structural arrangement requires that the spring member be compressed into its activated state while in this flat position, subject to fatigue and/or accidental release.

Another evacuator device is described in U.S. Pat. No. 4,460,354 to Weilbacher et al. This device also has the capability of being retained in its compressed, also referred to as activated, position. This is accomplished by a valve mechanism which seals off the evacuator to prevent loss of the vacuum that is being generated inside the evacuator. This valve allows the evacuator to be sealed off in a number of positions, including the fully compressed position. The resilient tensioning means, typically an elastomeric band, is maintained in its stretched, activated position during compression.

OBJECTS OF INVENTION

It is a principle object of this invention to provide a wound evacuator which can be maintained in a flat state without activating the tensioning member.

Another object of the invention is to provide an evacuator which is noncumbersome, easy to ship and store, and simple and inexpensive to manufacture and assemble.

A further object of this invention is to provide an evacuator in which it is easy to activate the tensioning member and the evacuator for use, and yet which cannot be accidently activiated.

A still further object of the invention is to provide an evacuator that will generate a low to moderate vacuum, and which further has the capability of being assembled to selectively provide varying vacuum capabilities simply and economically.

Another object of the invention is to provide an evacuator which is disposable and lightweight.

Another object of the invention is to provide an evacuator that does not require an external power supply, and yet is capable of being hooked up to an external power supply, such as wall suction, without collapsing, thus providing a full capacity container for fluid collection.

It is a further object of the invention to provide an evacuator in which the design is easily adaptable to various size evacuators depending upon the volume of evacuator desired.

SUMMARY OF THE INVENTION

The present invention accomplishes all of the above objects of invention. The wound evacuator of this device is comprised of a box-like internal body structure or hollow enclosure disposed within a fluid-tight, flexible outer pouch.

The pouch includes at least one valve opening which provides communication between the interior of the pouch and the atmosphere, or the interior of the pouch and a drainage tube. The pouch is comprised of an upper flexible film layer and a lower flexible film layer. Both layers are sealed along all their edges with a fluid and air-tight seal. One edge may include an opening through which the internal body structure is capable of being inserted. The opening can be sealed fluid tight by a closure means after the internal structure has been inserted. The flexible pouch is capable of expanding and collapsing as the internal body structure is expanded or collapsed.

The internal body structure may be comprised of four side panels each connected together by a hinge to form a box-like structure which is collapsible and expandable. This internal structure further includes a diagonal center panel on the internal side of the box-like structure. The diagonal center panel has a first end and a second end. The first end is hingedly connected to one of the hinges between two of the side panels. The center panel extends diagonally toward the oppositely located hinge. The second end of the center panel is connected to the opposite hinge by a tensioning member, such as an elastomeric member or a spring.

The evacuator may therefore be collapsed into a flat shape by compression of the box-like structure in a direction perpendicular to the center panel, this in turn stretches the tensioning member. Upon release of the compressive force, the tensioning member causes the internal structure to expand back into a box-like structure, thereby developing a negative pressure within the evacuator to draw fluid through a drainage tube and into the evacuator.

The center panel may advantageously be a two-part diagonal center panel, such that the first end and the second end of the center panel are two separate center portions connected in a sliding relationship with each other by a connecting portion. The two-part diagonal center panel may be fitted with sliding fingers on each panel forming the connecting portion. The connecting portion may include a latching means such that when the panels are slid together, they latch, causing the center panel to act as a single rigid unit. The two separate center portions may be either lockingly engaged with each other to functionally form a single panel or the two separate center portions may be in an unengaged state. When the center portions are lockingly engaged, and the internal structure is collapsed, the tensioning member is engaged, and therefore is stretched, thus activating the evacuator. When the center portions are in an unengaged state, and the internal structure is collapsed, the first end slides with the hinge to which it is hingedly attached, and the second end slides with the opposite hinge to which it is connected by the tensioning member. Therefore, when the two center panels are in their unengaged state, and the evacuator is collapsed, the tensioning member is also not in an engaged position, such that it is not caused to be stretched, and hence the evacuator can be collapsed and remain in a non-activated collapsed state without danger of unintentional activation.

Alternatively, the center panel may be a one-part panel. With a one-part center panel, the evacuator can be collapsed, thus stretching the tensioning member and activating the evacuator. However, with a one-part center panel, the evacuator cannot be collapsed in a non-activated state.

The evacuator with a two-part center panel, will preferably be assembled so that the two center panel portions of the internal structure are in their disengaged position. That way the evacuator can be packaged in its flat (yet non-activated) position which is less bulky. The evacuator can be shipped and stored in this condition. The evacuator may be packaged as a pre-sterilized item. When ready for use, the flat evacuator is removed from its package. A force parallel to the center panel may be applied to both ends of the center panel in order to slide the internal structure together. This force is applied until the internal structure is fully expanded and the two portions of the center panel have become lockingly engaged to each other. When it is time to initiate the drainage of the wound, a compressive force perpendicular to the center panel is applied to the evacuator until the evacuator is again in its flat position (this time with the tensioning member engaged, or stretched, therefore activating the evacuator). The air inside the evacuator is expelled to the atmosphere through the valve upon compression of the evacuator. Then the appropriate wound drainage tubing is applied to the valve, establishing communication between the interior of the evacuator and the drainage tubing. The appropriate tubing has already been placed in the wound site in accordance with standard wound drainage procedures. Upon release of the perpendicular compressive force, the tensioning member applies a force which causes the internal structure to expand back into its expanded box-like shape, hence developing a negative pressure within the evacuator to draw fluid through the drainage tubing and into the expanding evacuator.

BRIEF DESCRIPTION OF THE DRAWINGS

In order that the principles of the present invention may be readily understood, various embodiments of the present invention will be described with reference to the accompanying drawings, which form part of the original disclosure of this application, and wherein:

FIG. 17 is a top view of the first end of the center panel of the internal body structure of FIG. 7;

FIG. 18 is a side view of the first end of the center panel of FIG. 17;

FIG. 19 is a top view of the second end of the center panel of the internal body structure of FIG. 7;

FIG. 20 is a side view of the second end of the center panel of FIG. 19;

FIG. 21 is a top view of the first end of the center panel of FIG. 17 engaged to the second end of the center panel of FIG. 19;

DETAILED DESCRIPTION OF THE INVENTION

Figure 1:
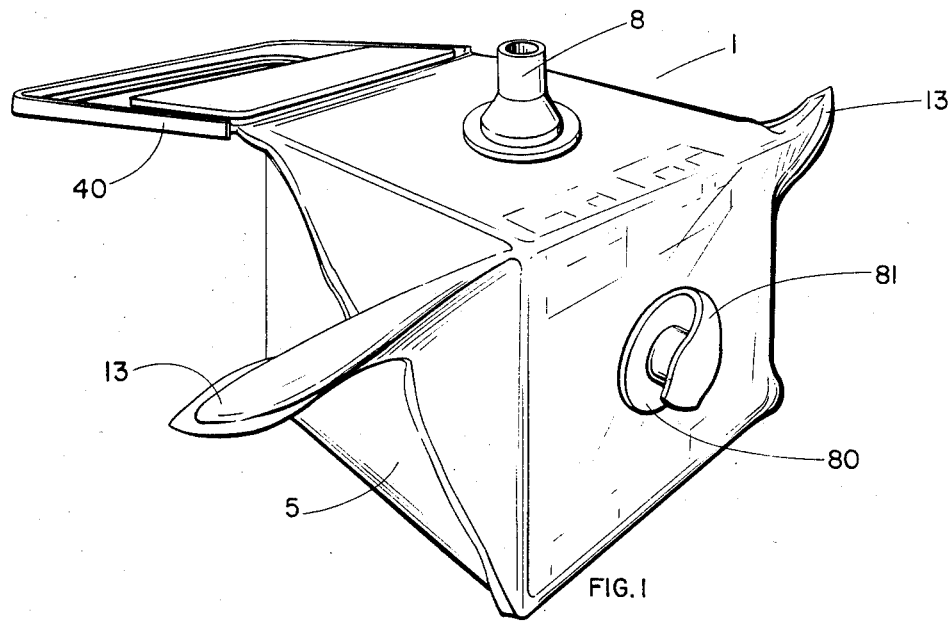
FIG. 1 is a perspective view of a particularly advantageous embodiment of the evacuator in its fully expanded and engaged box-like position.

The closed wound suction evacuator system 1 is illustrated in FIGS. 1-28. The evacuator 1 is comprised of a box-like internal body structure 15 or enclosure disposed within a fluid-tight, flexible outer pouch 5.

A particularly advantageous embodiment of the internal body structure 15 is illustrated in FIGS. 7 through 12. This structure 15 is comprised of four substantially flat, rigid side panels 17 or walls. Each side panel is consecutively numbered as 17a, 17b, 17c, and 17d. These four side panels 17 are each connected together by a hinge 16 to form a box-like structure which is collapsible and expandable. The four hinges are also consecutively numbered as 16a, 16b, 16c, and 16d. The internal structure further includes a substantially flat, diagonal center panel 18. The center panel 18 has a first end 19 and a second end 20. The first end 19 is hingedly connected at hinge 16a between side panels 17a and 17d. The center panel 18 extends diagonally toward the oppositely located hinge 16c. The second end 20 is connected to hinge 16c by a tensioning member. The tensioning member may be any suitable resilient structure, such as an elastomeric band 31.

Figure 10:
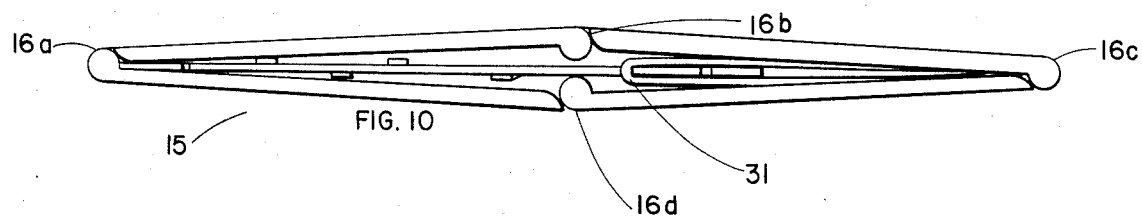
FIG. 10 is a front view of the internal body structure of FIG. 7 illustrating the structure in a fully collapsed and engaged position.

The internal body structure 15 may be collapsed into a flat shape, as shown in FIG. 10 by compression of the box-like internal structure 15 in a direction perpendicular to the center panel 18, hence stretching the tensioning member. Upon release of the compressive force, the tensioning member will cause the internal structure 15 to expand back into its box-like shape.

When the evacuator 1 is termed to be in an "engaged" position, this is herein defined to mean that the tensioning member is in position to be stretched upon collapse of the internal structure 15. If the evacuator 1 is in an "unengaged" position, the tensioning member is not in position to be stretched upon collapse of the internal structure 15. If the evacuator 1 is described as being "activated" it means the evacuator is in an engaged and collapsed position.

Figure 11:
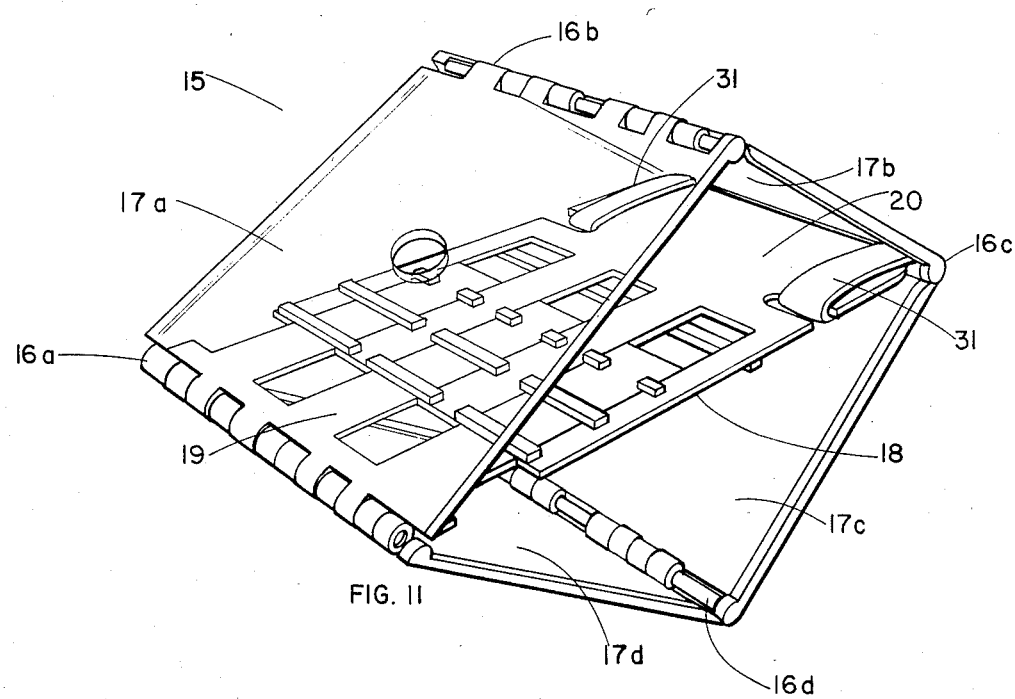
FIG. 11 is a perspective view of the internal body structure of FIG. 7, illustrated in a partially expanded (partially collapsed) and unengaged position.

The first end 19 and second end 20 of the center panel 18 are preferably two separate center portions connected in a sliding relationship with each other by a connecting portion 58. The separate first end 19 is illustrated in FIGS. 17 and 18, and the separate second end 20 is illustrated in FIGS. 19 and 20. The two separate center portions may be either lockingly engaged with each other, as shown in FIG. 21, to functionally form a single rigid panel, or the two separate center portions may be unengaged, although slidingly interconnected, as shown in FIG. 11. When the two separate portions are lockingly engaged to form a single-acting panel, the tensioning member is also engaged. Hence, upon collapse of the structure 15, the tensioning member is stretched, hence enabling activation of the evacuator 1. When the two separate center portions are unengaged, the tensioning member is also in an unstressed position. Therefore, when the structure 15 is collapsed, the first end 19 of the center panel 18 slides toward hinge 16a to which it is hingedly attached, and the second end 20 slides toward hinge 16c, to which it is connected by the tensioning member, see FIG. 11. Therefore, when the two center panels are in their unengaged state, and the structure 15 is collapsed, it can remain in a nonactivated collapsed state without exerting any continued compressive force on the evacuator 1 and without the tensioning member being stretched.

The connecting portion 58 between the first end 19 and second end 20 includes at least one extending finger 50 on one of the center panel portions positioned in sliding relation between a corresponding finger receiving opening 51 in the other center panel portion. A particularly advantageous embodiment of the center panel 18 is illustrated in FIGS. 7-12 and 17-21. The first end 19 (See FIG. 17 and 18) may include one or more (three are shown) extending fingers 50, and the second end 20 includes corresponding finger receiving openings 51. The finger receiving openings 51 are bounded by side walls 52. The openings 51 may include a plurality of alignment extensions. These extensions may be in the form of alignment bars 55 which extend completely across the openings 51, or they may be alignment buttons 56 which just protrude from either side of the openings 51. The alignment bars 55 or buttons 56 may be alternately positioned on the top side and bottom side of center panel 18. The alignment bars 55 prevent the side walls 52 of the openings 51 from spreading apart, hence forming a more sturdy structure. Both the alternating bars 55 and buttons 56 keep the sliding fingers 50 aligned in the plane of the center panel 18 and prevent them from popping or flexing out of position.

Figure 12:
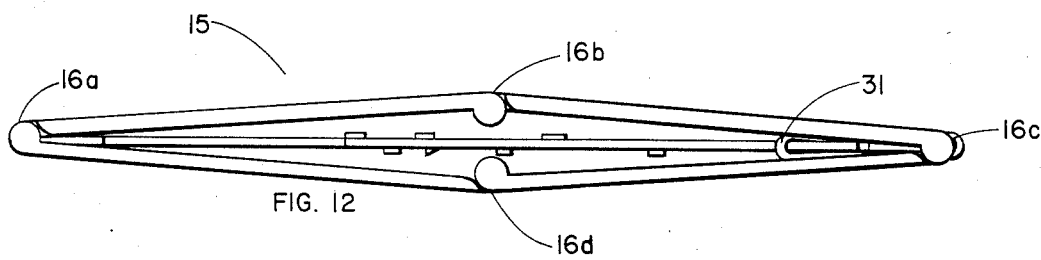
FIG. 12 is a front view of the internal body structure of FIG. 7 illustrated in a fully collapsed and unengaged position.

FIG. 12 shows the center panel in its unengaged position with the internal body structure 15 in its collapsed state. When assembled and collapsed in the unengaged position, the first end 19 and the second end 20 assume an extended configuration with the first end attached to hinge 16a and the second end 20 held to hinge 16c by a slight tension of the tensioning member. The fingers 50 of the one end are partially engaged into the openings 51 of the other end, keeping the two parts in alignment while in the collapsed, unengaged position. FIG. 11 shows the internal structure 15 in a partially expanded position, illustrating the first end 19 and second end 20 sliding toward each other.

Figure 7:
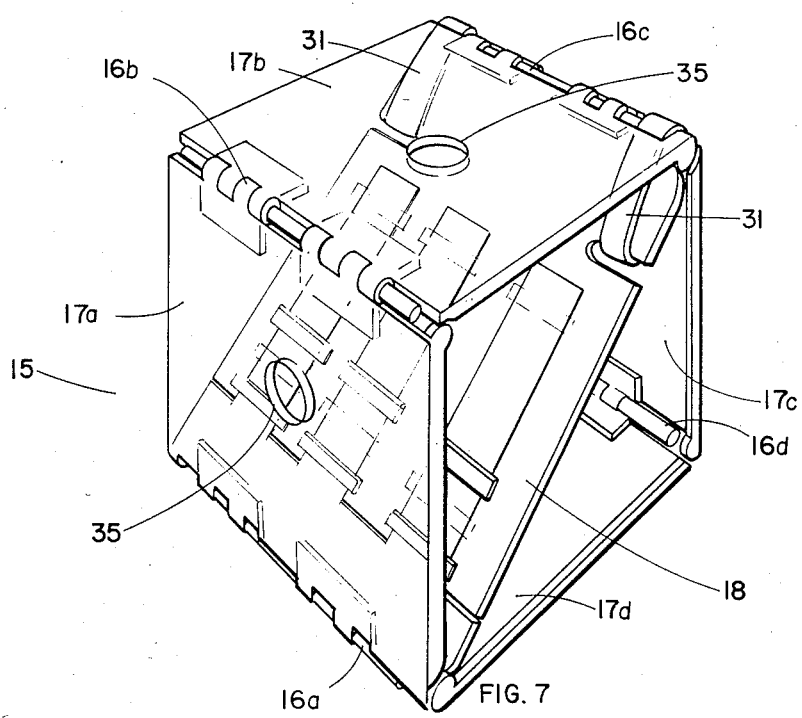
FIG. 7 is a perspective view of a particularly advantageous embodiment of the internal body structure for the evacuator of FIG. 1 illustrating the structure in its engaged fully expanded position.
Figure 8:
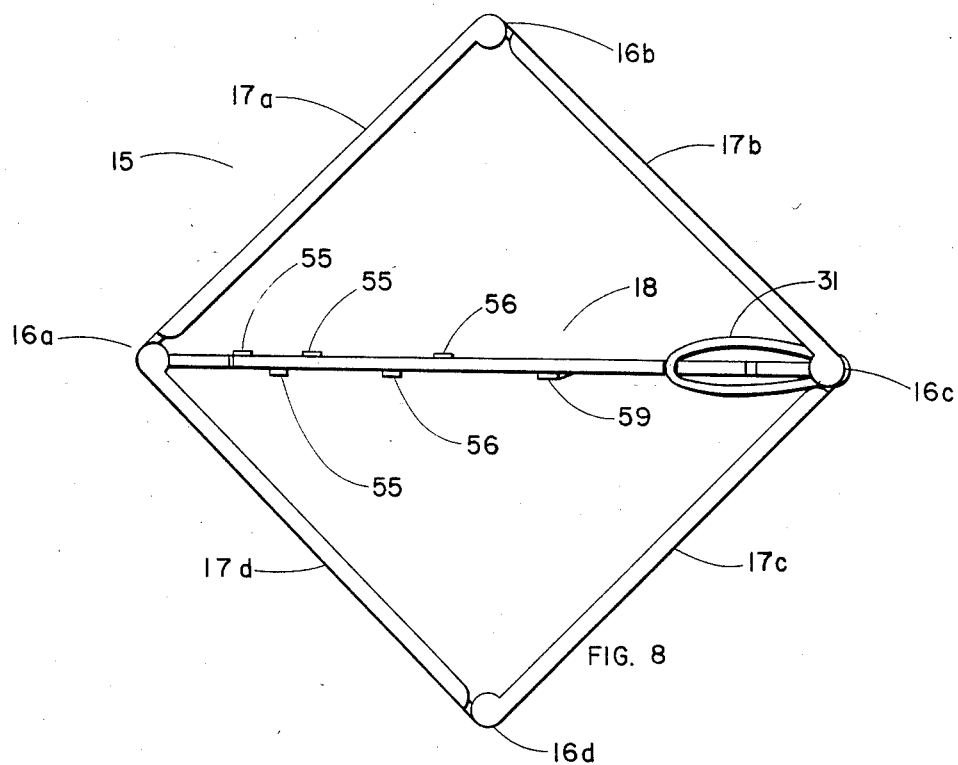
FIG. 8 is a front view of the internal body structure of FIG. 7 illustrating the structure in its fully expanded and engaged position.
Figure 9:
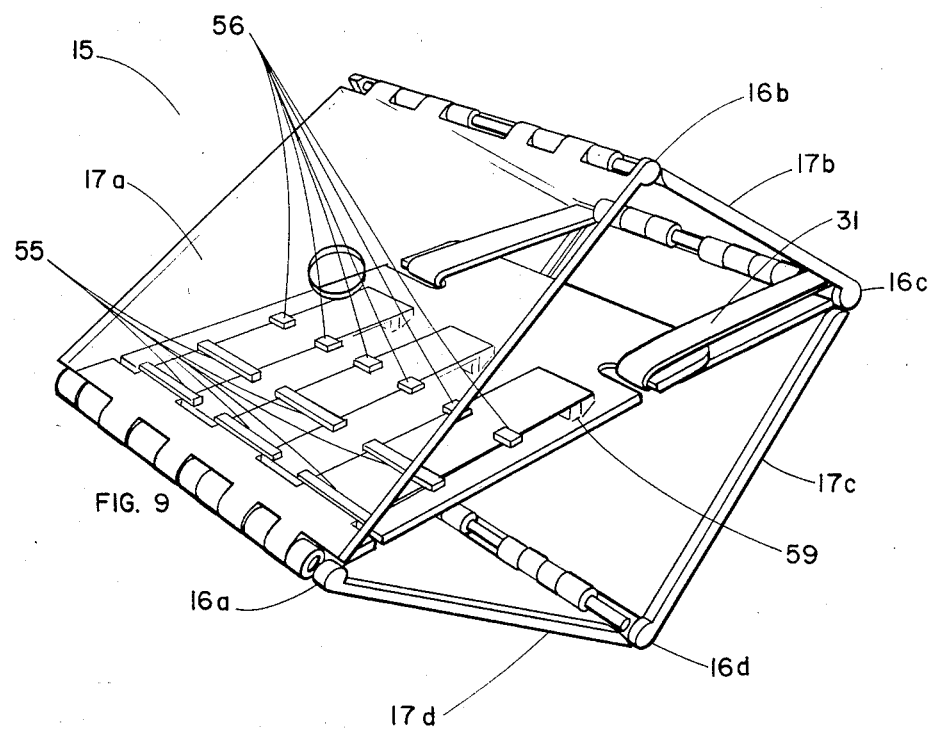
FIG. 9 is a perspective view of the internal body structure of FIG. 7 illustrating the structure in a partially collapsed (or partially expanded) and engaged position.

The sliding mechanism of the center panel 18 further includes a latching means to engage the two center panel portions together. In general, the latching means may be any suitable means for interlocking the first end 19 to the second end 20 so that they are able to act as a single panel. FIG. 7 illustrates the internal structure 15 fully expanded with the first end 19 and second end 20 engaged. A particularly advantageous embodiment for the latching means (as shown in FIGS. 17 to 21) includes a latch bar 59 located toward the far end of each opening 51, and extending across the top side 18a of each of the openings 51, and a correspondingly located protrusion 60 on each of the fingers 50 for locking against the latch bar 59. Each protrusion 60 includes a sloped surface 62 which slopes up from the surface of the finger 50 to allow the protrusion to slide under the latch bar 59, as the two center portions are pushed into engagement with each other. The protrusion further includes a flat shoulder 61 which drops down from the peak level of the slope 62 back to the surface of the finger 50. The sloped surface 62 may flatten out after it reaches its peak before the flat shoulder 61 drops down, as shown in FIG. 18. The flat shoulder 61 locks against the latch bar after the protrusion has passed underneath the latch bar 59, thereby engaging the two center portions together.

Figure 13:
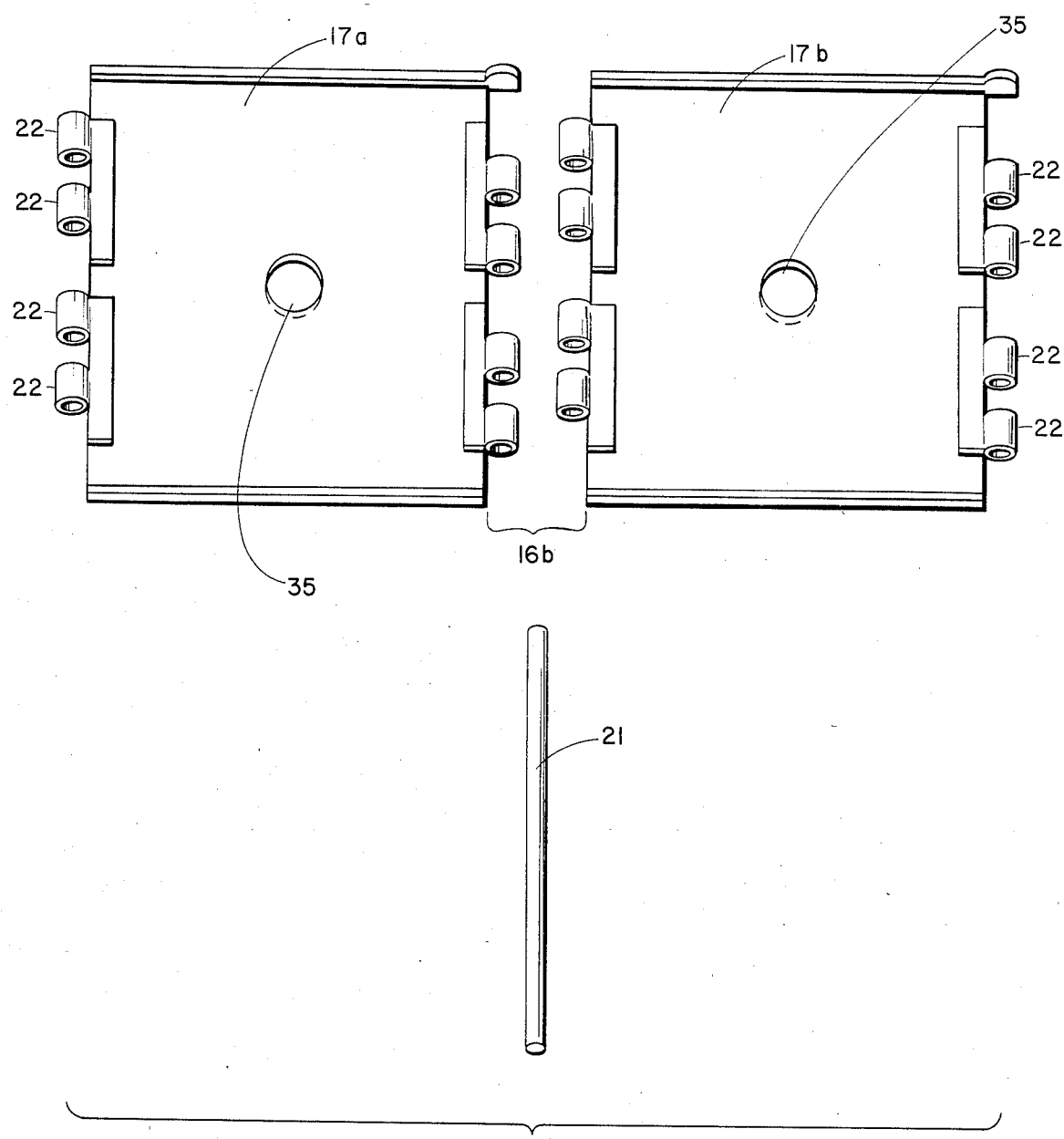
FIG. 13 is a top perspective view of two of the side panels of the internal body structure and their connecting hinge rod illustrated disassembled from each other.
Figure 14:
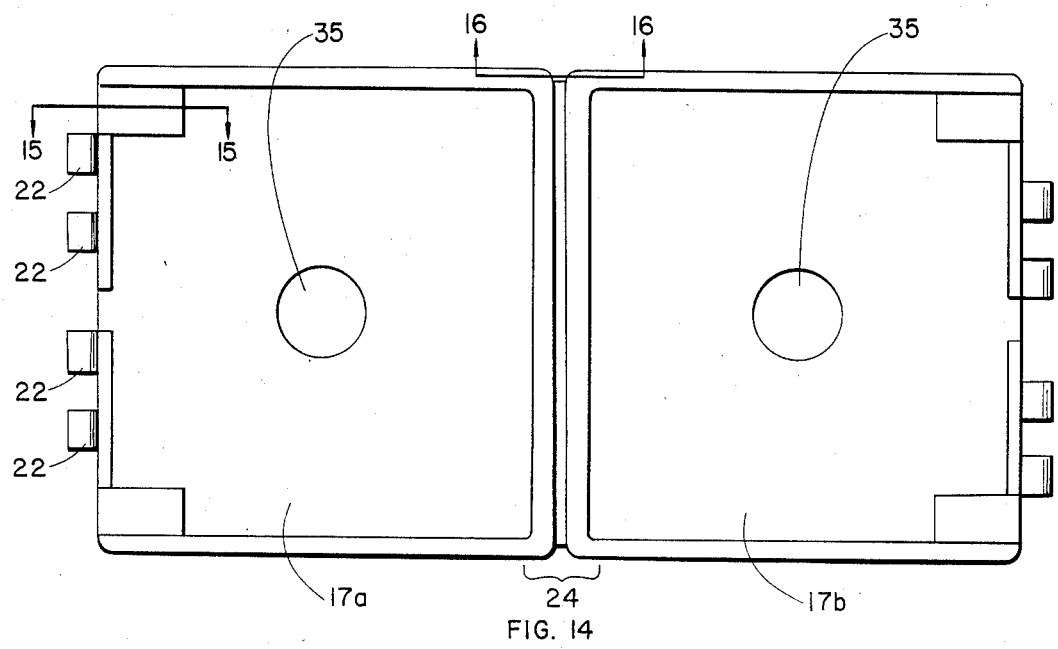
FIG. 14 is a top view of an alternate embodiment of two of the side panels of the internal body structure with an integral hinge connecting the two panels.
Figure 15:
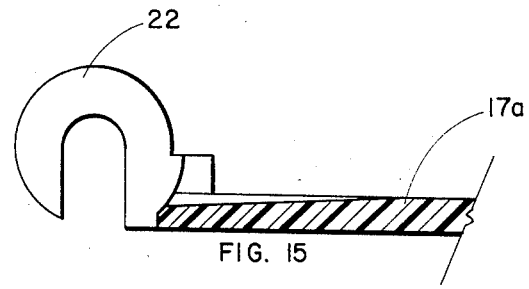
FIG. 15 is an enlarged sectional view of the side panels of FIG. 14 taken along lines 15—15 of FIG. 14 and illustrating the configuration of one of the interlocking projections of the side panel of FIG. 14.
Figure 16:
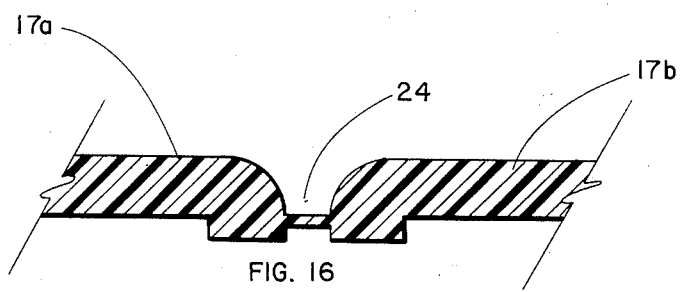
FIG. 16 is an enlarged sectional view of the side panels of FIG. 14 taken along lines 16—16 of FIG. 14 and illustrating the integral hinge configuration.
Figure 22:
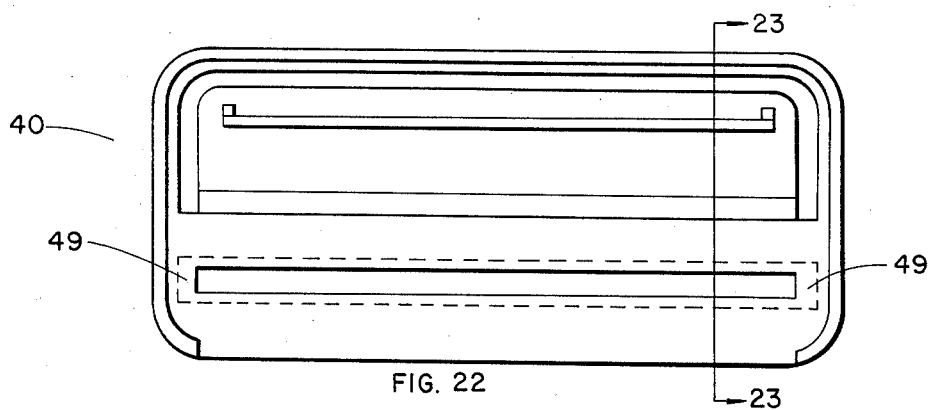
FIG. 22 is a top view of a particularly advantageous embodiment of the closure mechanism for the evacuator.
Figure 23:
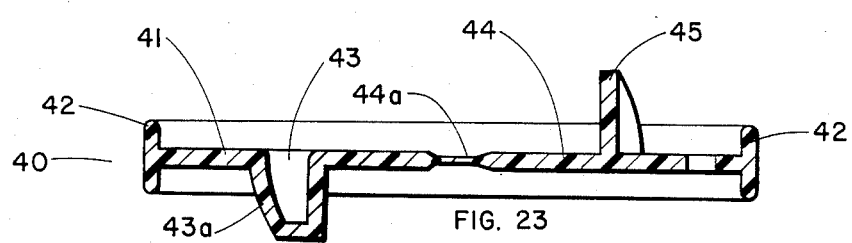
FIG. 23 is a side view of the closure mechanism of FIG. 22.
Figure 24:
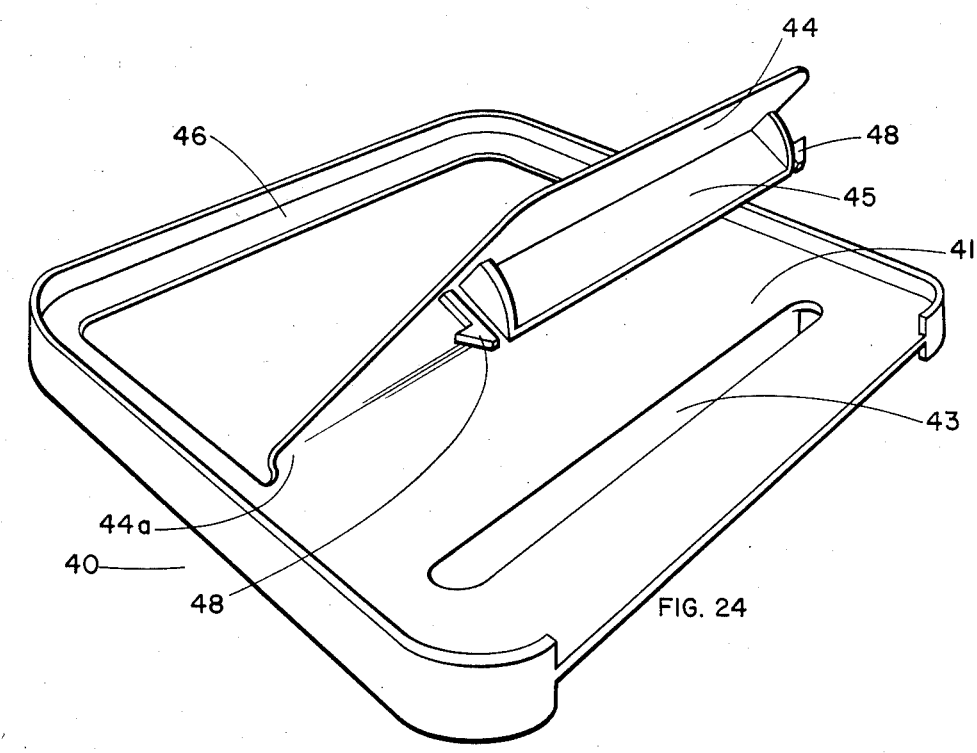
FIG. 24 is an enlarged perspective view of the closure mechanism of FIG. 22.

The hinge means 16 between the panel members 17 may utilize any suitable mechanism for making a hinge connection. One type of suitable hinge means is shown more particularly in FIG. 13. FIG. 13 illustrates two of the side panels 17a and 17b and hinge means 16b. Hinge means 16b includes a series of corresponding interlocking tubular projections 22 which extend from panels 17a and 17b. When the two panels 17a and 17b are brought together, such that the projections 22 are actually interlocked, a tubular channel 23 is provided through which an elongated pin member 21 is inserted, thereby providing a hinge means. The tubular projections 22 may be integrally formed with each respective panel 17 or separately adhered to or affixed to the panel 17 by any convenient means.

Each hinge means 16 may incorporate this type of hinge mechanism between the side panels 17. The first end 19 of the center panel 18 may also include interlocking tubular projections 22 which are spaced accordingly to interlock with the interlocking projections 22 of side panels 17a and 17d. This allows the first end 19 of the center panel 18 to be hingedly connected at one of the hinge means 16 between two of the side panels 17.

The side panels 17 and center panel 18 may be made of any suitable rigid material, but it is preferable to use a light-weight material such as plastic. Whatever material is used, it is important not to have any sharp or rough surfaces on the internal body structure 15 which could accidentally penetrate the flexible outer pouch 5. The interlocking projections 22 may also be made of any suitable material such as plastic. The projections 22 may be manufactured integrally with the panels 17 and 18, or they may be manufactured separately and then suitably adhered or connected by any convenient means to the panels. The hinge rod 21 may be made of metal, although again, any suitable material could be used.

Another embodiment for hinges 16b and 16d is illustrated in FIGS. 14 to 16 and 25. Side panels 17a and 17b may be molded in one piece with integral hinge 24 as the connecting hinge 16b. Likewise side panels 17c and 17d may be molded in one piece with an integral hinge 24 as the connecting hinge 16d. The side panels 17 of this embodiment could be molded from polyprophylene with the integral hinge 24 being of such a reduced thickness, so as to act as a hinge. In the particular embodiment shown in FIG. 25, hinges 16a and 16c are of the hinge pin or hinge rod style previously described. The ends of the side panels which meet to form hinges 16a and 16c still include interlocking projections 22 which mate to form a tubular channel 23 for the hinge rod 21. This style allows the first end 19 of center panel 18 to still be conveniently hinged at hinge 16a. Also the rod style of hinge at hinge 16c is convenient for attachment of a suitable tensioning means. The center panel 18 would still preferably be made from a rigid plastic material.

The tensioning means may be any suitable resilient structure, such as an elastomeric band 31 or a resilient spring 32. The embodiment of the internal body structure 15 illustrated in FIGS. 7 to 12 show an elastomeric band 31. Band 31 could be made from any suitable resilient material, such as rubber or latex. The embodiment illustrated in FIGS. 2 and 7-12 utilizes two elastomeric bands 31, one on the front side and one on the rear side of the second end 20 of the center panel 18. Each band 31 is hooked about the respective end of hinge rod 21 of hinge 16c. The other end of each band 31 is hooked to an attachment means, such as a notch 57 on the second end 20 of the center panel 18. FIGS. 18 and 20 illustrate a plurality of notches 57 along the front and rear sides of the second end 20. The band 31 can be selectively placed in the appropriate notch to regulate the amount of tension the band 31 will be placed under when the internal body structure is collapsed, since this will regulate how far the tensioning means is stretched. In this manner, it is possible to vary, or regulate, the force of the vacuum draw which will be created during use of the evacuator 1. This can also be varied by the characteristics of the elastomeric band 31 itself, such as its length, thickness, and width.

It would be possible to use just one resilient structure for the tensioning means, if desirable. This single structure would preferably be located centrally on the hinge rod 21 and second end 20 of the panel 18, to provide a balanced pull. More than two resilient structures could also be utilized, if desirable.

Figure 25:
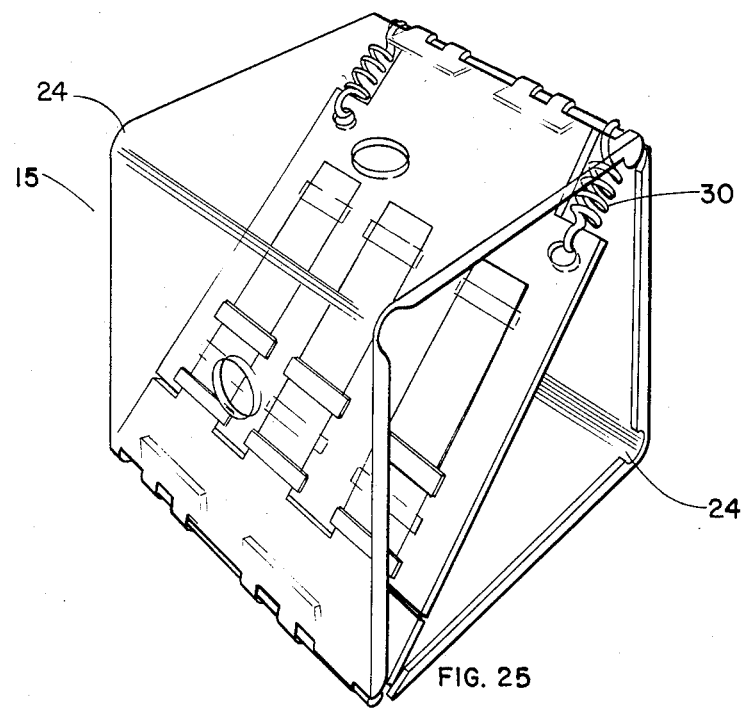
FIG. 25 is a prespective view of an alternate embodiment of the internal body structure utilizing the side panel embodiment of FIG. 14.

FIG. 25 illustrates the tensioning means as a spring 32. The spring 32 is connected to the hinge rod 21 at hinge 16c by one end of the spring, with the other end of the spring appropriately hooked to the second end 20 of the center panel 18. The spring also could be chosen to vary its tension characteristics depending on the force which is desired.

The internal body structure, when assembled, is placed inside the pouch 5. The pouch is illustrated in FIGS. 1 through 6. It may be made from any thin and flexible, yet strong fluid-tight material. Vinyl or ethylene vinyl acetate are examples of suitable materials, although other appropriate materials may be used. The pouch 5 must be able to accommodate the internal structure 15 in both its fully expanded and fully collapsed form, as well as any partially expanded or collapsed position therebetween. The pouch 5 is preferably not too much larger than it has to be in order to accommodate the expanding or collapsing internal structure 15 so that the pouch 5 properly expands and collapses as the internal structure 15 does.

The pouch 5 includes at least one valve opening 8 which provides communication between the interior of the pouch and atmosphere, or the interior of the pouch and an appropriate drainage tube. The valve 8 is sealed to the pouch 5. A communication hole is provided in the pouch to allow the communication between the interior of the pouch 5 and the valve 8. In addition, at least one panel 17 may include a hole 35 positioned in the panel 17 so that it will be aligned beneath the valve 8 to aid in drawing fluids through the valve and into the evacuator chamber. Preferably, *each* panel 17 has a suitably positioned hole 35, so that no matter which way the internal structure 15 is inserted into the pouch 5, and no matter which panel 17 ends up positioned beneath the valve 8, a suitable hole 35 in a panel 17 will be appropriately positioned beneath the valve 8.

Figure 2:
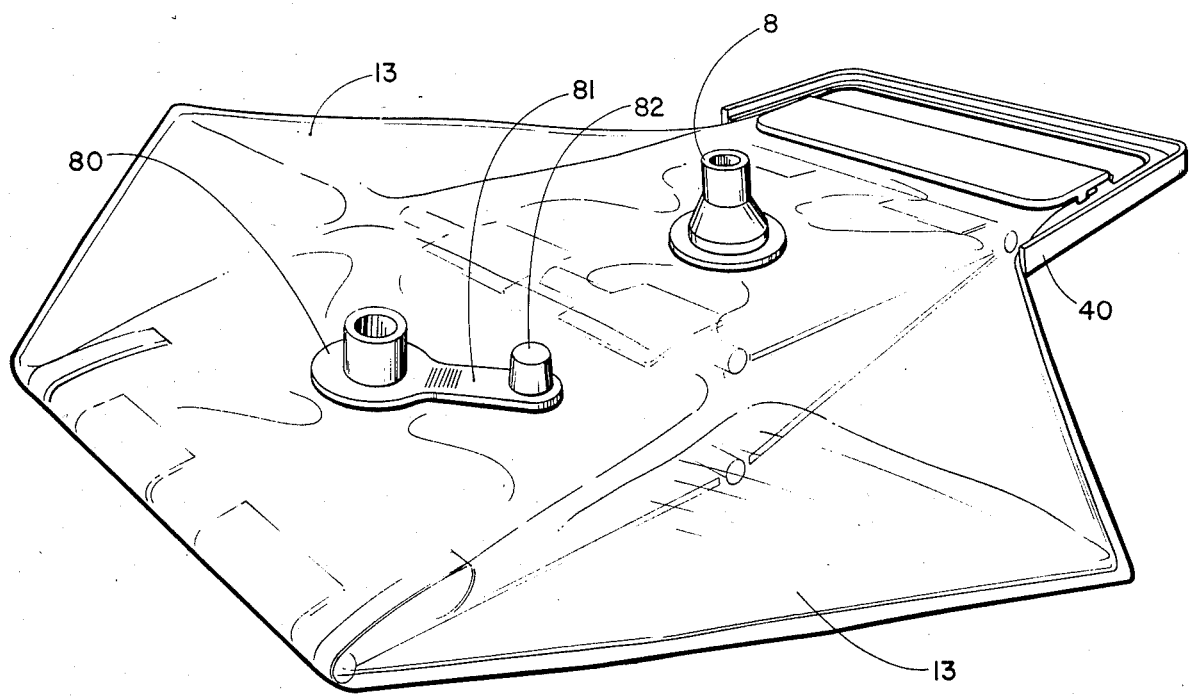
FIG. 2 is a top view of the evacuator of FIG. 1 shown in its fully collapsed and unengaged position.
Figure 5:
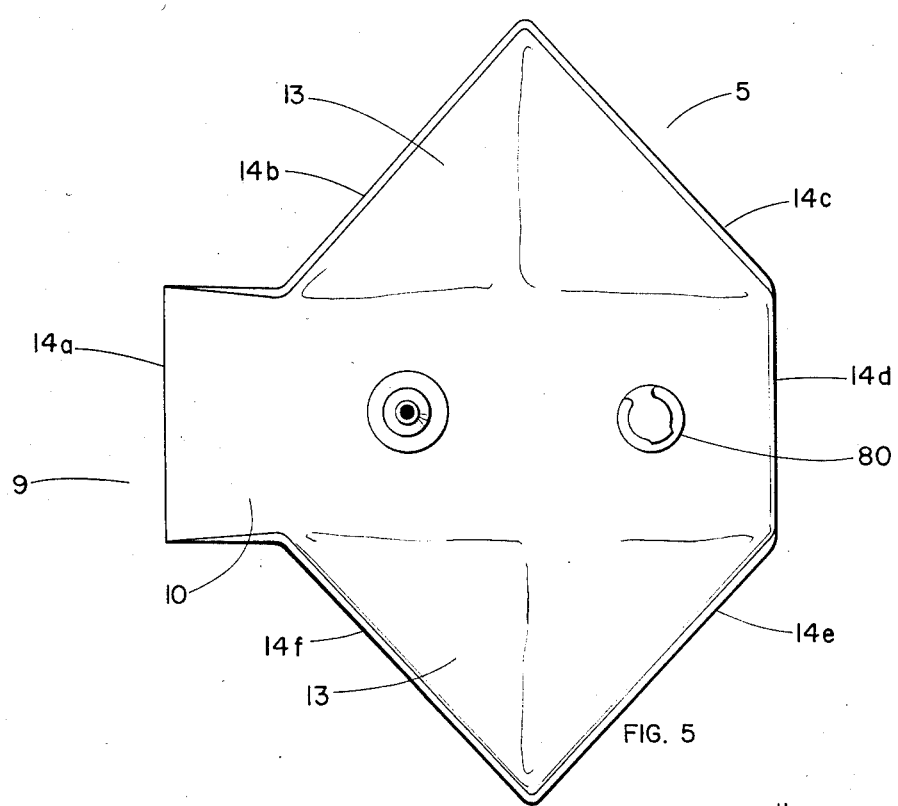
FIG. 5 is a top view of the evacuator pouch of FIG. 1.
Figure 6:
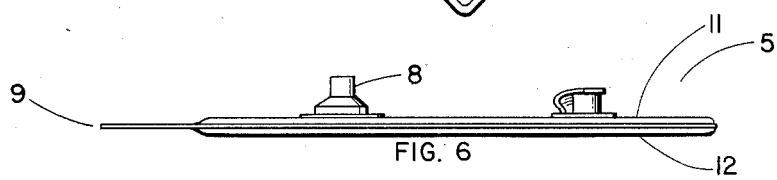
FIG. 6 is a side view of the pouch of FIG. 5.

A convenient geometry for the pouch 5, which would be suitable for the cube-shaped internal structure 15, is a substantially six-sided configuration wherein the six-sides are designated 14a, b, c, d, e, and f such as shown in FIGS. 5 and 6. Side 14a includes an opening 9 through which the internal body structure 15 is insertable. The pouch includes an upper and lower layer 11 and 12 which may be formed by folding a single sheet of the pouch material to form folded edge 14d. The upper layer 11 and lower layer 12 may then be sealed to each other by a fluid-tight seal, such as a heat seal about edges 14b, 14c 14e and 14f leaving edge 14a open to form opening 9. The seal may be conveniently applied using an RF die and high frequency radio waves. Sides 14a and 14d are paralled to each other such that the internal body structure 15 can be conveniently located in the pouch 5. Although the pouch could be designed to allow the internal structure 15 to be inserted in a variety of ways, the design shown allows for the flattened or compressed structure to be inserted through the opening 9 with either hinge 16a or 16c entering the opening 9 first. The collapsed structure 15 takes up a rectangular space in the pouch as shown in FIG. 2, leaving two triangular side portions 13. The triangular portions 13 are partially taken up, when the internal structure 15 is expanded, as shown in FIG. 1, but a portion of the triangular portions 13 still may protrude. The shape of the pouch can be designed in a variety of ways to allow for the expansion or collapse of the evacuator 1.

Once the internal structure 15 is inserted in the pouch, the opening 9 may be sealed fluid-tight. This can be done by a variety of methods. It may be convenient to extend side 14a which includes opening 9, to form an extended pouch portion 10 as shown in FIG. 5. One such method of sealing the pouch could be to heat seal the pouch across the extended portion 10, hence sealing off the opening 9. Another method would be to provide a closure means 40 such as is illustrated in FIGS. 1 to 4 and 22 to 24 to sealingly lock off the opening 9 in pouch 5. A convenient closure means 40 includes a platform member 41 for receiving the extended pouch portion 10. The platform includes an elongated groove 43 with a recessed container 43a. The closure means 40 further includes a flap member 44. The flap member 44 may be connected to the platform 41 by a flap hinge 44a. The flap 44 includes a protruding elongated ridge 45. The extended portion 10 of the pouch 5 is placed over the platform 41 and over the groove opening 43. The flap member 44 is then positioned so that the protruding ridge 45 is received in the groove 43, hence pushing the extended portion 10 of the pouch 5 down in the groove 43 and into the recessed container 43a, therefore sealing off the opening 9 in the pouch 5.

It may be desirable to have a means for locking the flaps 44 in the recessed container 43a. Therefore, the ridge 45 may include a side extension with a locking protrusion 48 slightly spaced away from either side of the ridge. The space allows for the extension to bend toward the ridge 45 slightly, hence allowing the protrusion portion of the extension 48 to snap under an undercut ledge 49 of the recessed container 43a. This prevents the closure means 40 from being easily opened.

The closure means 40 may include handle portion 46. The handle 46 is convenient for carrying the evacuator or for hanging it up conveniently during use.

The closure means may be made of polypropylene or any other suitable material. The closure means may be conveniently molded so that the flap 44 and platform 41 are connected by an integral flap hinge 44a, although other means of forming the closure means are suitable.

A different kind of handle could also be provided if desired. Although not illustrated, a handle could be attached to one of the side flaps 13 of the pouch 5. A hole could be formed through both pouch layers at the very tip of the triangular portions 13. Then a heat seal could be placed across the flap between the hole and the rest of the flap 13 which would prevent the hole from having any communication with the interior of the pouch 5. Then, any convenient handle or hanging means could be clamped to the tip of the triangular portion 13 or through the hole in triangular portion 13.

Figure 3:
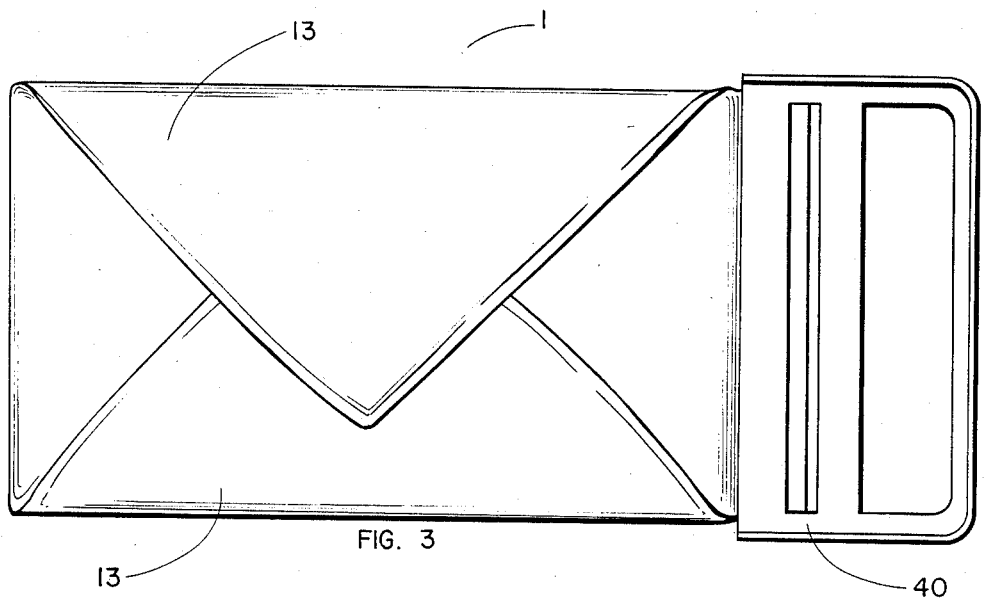
FIG. 3 is a bottom view of the evacuator of FIG. 2 shown in its fully collapsed unengaged position with the two triangular side portions of the pouch folded over onto the underneath side of the flat evacuator.

The evacuator 1 will preferably be assembled so that the internal body structure 15 is in its flat and unengaged position, such as is shown in FIG. 12. This allows the evacuator 1 to remain flat without applying any external compressive force. The flat, unengaged internal structure is inserted into the opening 9 of the pouch 5. The extended portion 10 of the pouch 5 is sealed by the closure means 40 to create a fluid tight evacuator 1 as illustrated in FIG. 2. The triangular portions 13 of the pouch 5 may be folded to the underneath side of the flap evacuator 1, as shown in FIG. 3. The closure means 40 may be folded back onto the top side of the flat evacuator 1 such that the opening created by the handle portion 46 fits over the valve 8. Although FIG. 4 does not illustrate the closure means 40 folded back, it can be seen from FIG. 4 that this could be done. This creates a very compact flat device for packaging, shipping, and storing. The evacuator can be stored indefinitely in this flat, unengaged state, hence not activating or stretching the tensioning means, but allowing the tensioning means to be in its rest position even if the evacuator is collapsed.

It is possible to retain the evacuator in its flat and engaged and activated state, if desirable. With the engaged and activated internal structure 15 enclosed in the pouch 5, the evacuator may be manually held in a flat condition, or the evacuator may be held by a mechanical means to prevent the pouch 5 from expanding, and hence retaining the evacuator in its collapsed, yet activated position. For example, the triangular side portions 13 of the pouch 5 which extend beyond the internal structure 15, can be folded over underneath the evacuator (such as in FIG. 3). A mechanical means (not shown), such as a snap, could be provided on the triangular portions 13 to hold them together in their folded under position. It is noted that when the evacuator 1 is held in this pre-activated, flat condition, the tensioning member is also in its stretched, activated condition.

The evacuator 1 is preferably shipped in the flat, non-activated position; however, it may also be shipped in the flat, pre-activated condition or in its expanded, activated or non-activated, position, if desirable.

The evacuator 1 is preferably presterilized by any appropriate sterilizing method, such as ethylene oxide sterilization. Once the evacuator 1 is sterilized, the pouch should not be reopened, as this would break the sterile barrier and cause contamination of the sterile evacuator 1.

When ready for use, the evacuator 1 is removed from any packaging material. The handle 46 is unfolded and the triangular side portions 13 of the pouch 5 are also unfolded. The evacuator then appears as illustrated in FIG. 2. The evacuator 1 may be held at hinges 16a and 16c. A compressive force is applied parallel to the center panel 18 by manually applying force at hinges 16a and 16c to cause the internal structure 15 to expand from an unengaged flat position (FIG. 12) to an unengaged partially expanded position (FIG. 11) to a fully expanded engaged position (FIG. 7). As the fingers 50 and finger receiving openings 51 approach the limit of their travel toward each other, the latch protrusions 50 slide under the latch bars 59 and easily and firmly click the center panel 18 into its latched position. The fully expanded engaged evacuator 1 is illustrated FIG. 1.

When it is time to initiate the drainage of the wound, a compressive force is applied perpendicular to the center panel 18 by manually applying a compressive force at hinges 16b and 16d until the evacuator is again in a flat position, this time with the tensioning member engaged or stretched, therefore activating the evacuator. The internal structure moves from its engaged fully expanded position (FIGS. 7 and 8) to a partially collapsed engaged position (FIG. 9) to a fully collapsed and engaged position (FIG. 10). The air inside the evacuator 1 is expelled to the atmosphere through the valve 8 and the pouch 5 is flattened out.

The appropriate wound drainage tubing is then applied to the valve 8, establishing communication between the interior of the evacuator 1 and the drainage tubing. The drainage tubing is then, or already has been, appropriately placed in the wound site in accordance with standard wound drainage procedures.

Upon release of the perpendicular compressive force, the tensioning member applies a force which causes the internal structure 15 to expand back into its expanded box-like shape. As the tensioning member within the evacuator 1 pulls on the center panel 18, hinges 16a and 16c are drawn toward each other, forcing hinges 16b and 16d outward and increasing the internal volume of the evacuator 1, hence developing a vacuum within the evacuator 1 to draw fluid through the drainage tubing into the expanding evacuator 1.

Figure 4:
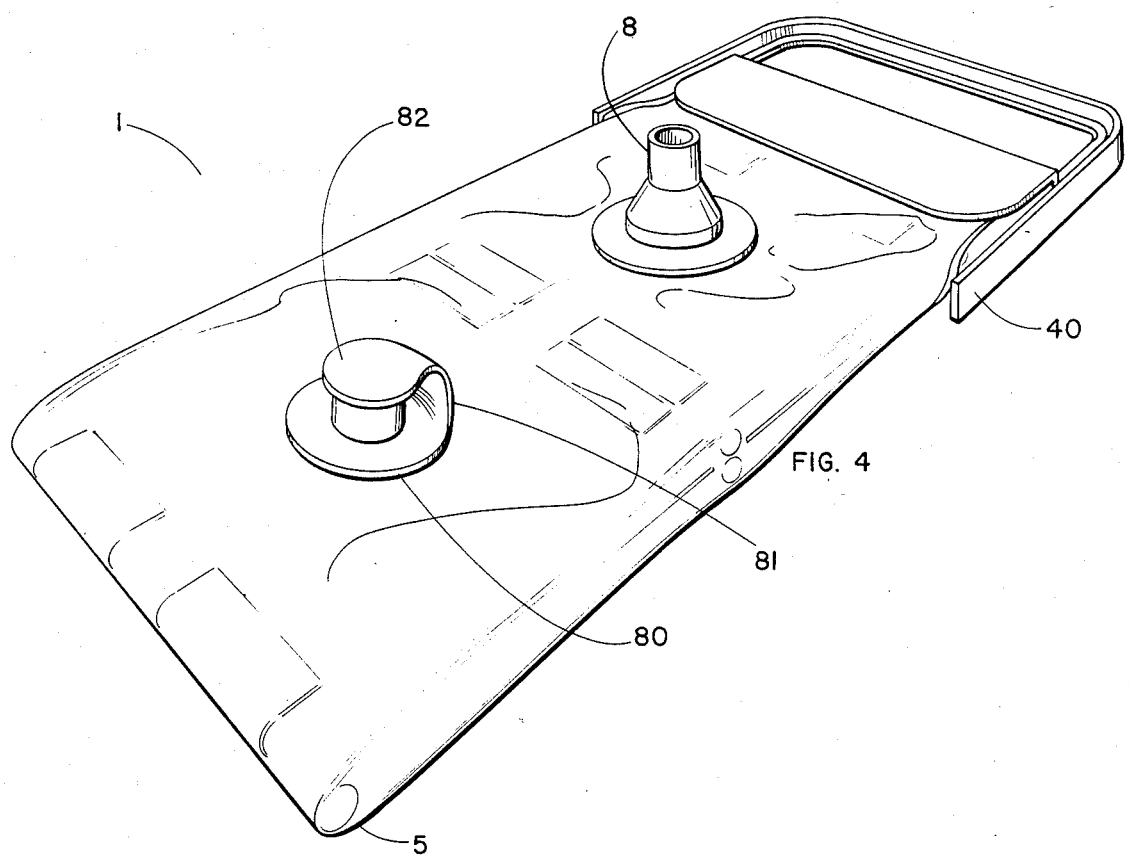
FIG. 4 is a perspective view of the evacuator of FIG. 3 shown in its fully collapsed unengaged position, and shown with the triangular portions folded underneath the evacuator, and with the combination closure/handle mechanism folded back onto the top of the evacuator.

The pouch 5 may include a second valve 80 as shown in FIGS. 1 and 2 and 4. The valve 80 includes a closure cap 82 connected by connecting strip 81. A communication hole is provided in the pouch 5 to allow the communication between the interior of the pouch 5 and the valve 80. As with valve 8, the valve 80 is preferably positioned so as to be aligned over a hole 35 in a panel 17 to establish better communication between the valve 80 and the interior of the evacuator.

When second valve 80 is incorporated in the evacuator assembly, the wound drainage tubing may be applied to valve 8 prior to compressing and activating the evacuator. If the wound drainage tubing has already been placed in the wound, the tubing may be clamped off to prevent fluid flow through the tubing. The closure cap 82 may be removed from valve 80 and the evacuator compressed to a flat, activated position. The air inside the evacuator 1 is then expelled to the atmosphere through valve 80 as the evacuator 1 is flattened out. The closure cup 82 is then replaced to close off valve 80 and the wound tubing unclamped for the self-contained evacuator to draw fluids from the wound.

The valve 80 may also be used as a pouring spout to empty the contents of the evacuator 1 which have been drawn into the evacuator 1 during the drainage of the wound. With second valve 80, this enables the fluids to be emptied through valve 80, hence the wound tubing does not have to be disconnected from valve 8 in order to empty the fluids.

Another feature of this evacuator 1 is, that in its expanded, engaged position, it can be connected by suitable tubing to an external vacuum source, such as wall suction, through second valve 80, to provide suction by an outside means to collect fluid. The evacuator is still connected to the wound via the drainage tubing connected to valve 8. With many prior art collapsible, self-contained evauators, wall suction causes the flexible container to collapse, and hence not as much fluid can be collected. With the internal structure 15 in its engaged position, the center diagonal panel 18 helps to create a more rigid structure. The structure will only collapse if a compressive force perpendicular to the center panel 18 is applied. Therefore, this evacuator can not only be used as an independently operable, self-contained evacuator, but it can also effectively be hooked up for use with an outside suction source. This permits use of this device as a vacuum collection bottle during surgery, then upon emptying and re-activating, it can remain as a patient wound suction device. With some obvious changes in proportion, the device can also be used as a wall suction cannister which can be shipped flat, to be expanded at the time of use. Other known suction cannisters are rigid assemblies that are bulky to ship and store.

The evacuator 1 may be manufactured in any appropriate size. It may be sized to provide such convenient volumes of 200 ml, 400 ml, 800 ml, or any other appropriate desirable size. In addition, markings (not shown) can be provided on the evacuator to determine the volume of fluid collected.

Since the internal volume of the expanded evacuator 1 will be a maximum when the hinged edges of the side panels 17 all have an included angle of 90° the engaged center panel 18 is preferably of such a length that it will limit the expansion of the device to that point and permit no further expansion. This is the preferred relationship which can be adapted according to the size evacuator desired. The theoretical amount of volume draw is the difference between the volume occupied when fully collapsed and the volume occupied when fully expanded. The center panel, when engaged as shown in FIG. 21, may conveniently be a substantially flat, rectangularly shaped panel.

The side panels 17 as illustrated in FIGS. 1–14 and 25 are substantially square. The square side panels provide a cube-shape upon full expansion and provide an efficient use of materials to achieve a given volume. However, if the side panels were taller than they were wide (or vice versa) the device would still function as described. The pouch 5 is then sized accordingly to accommodate the internal body structure 15.

Figure 26:
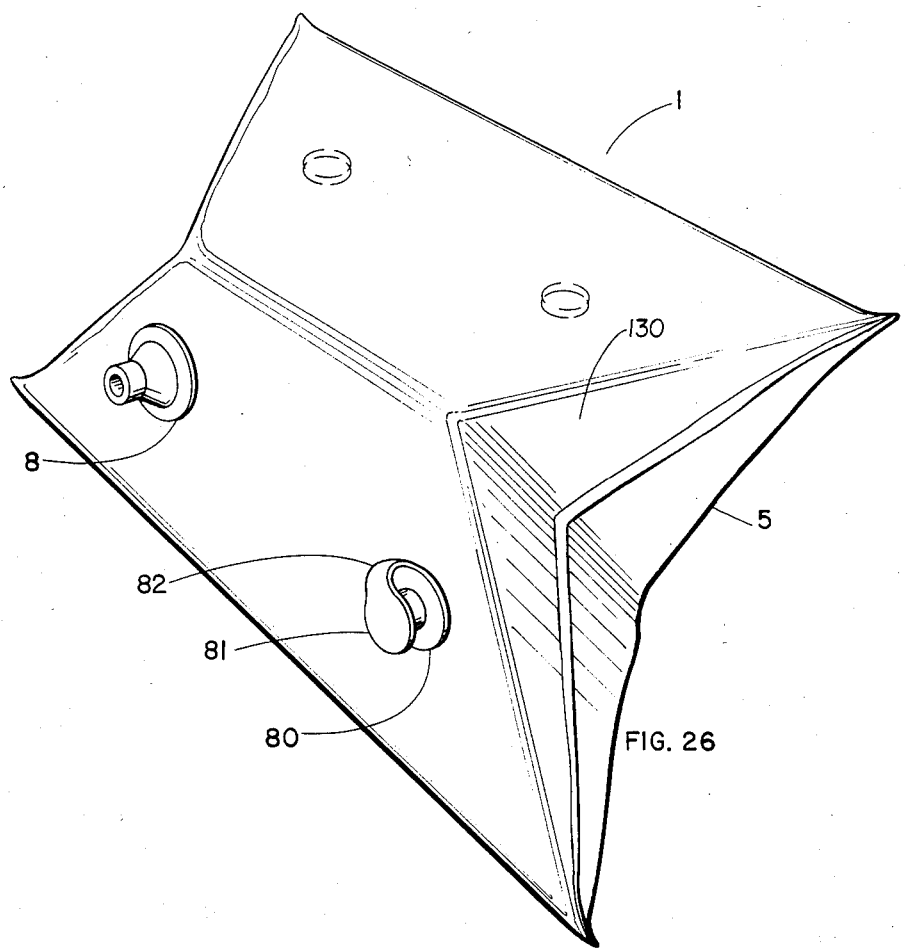
FIG. 26 is a perspective view of another particularly advantageous embodiment of the evacuator in its fully expanded and engaged box-like position.
Figure 27:
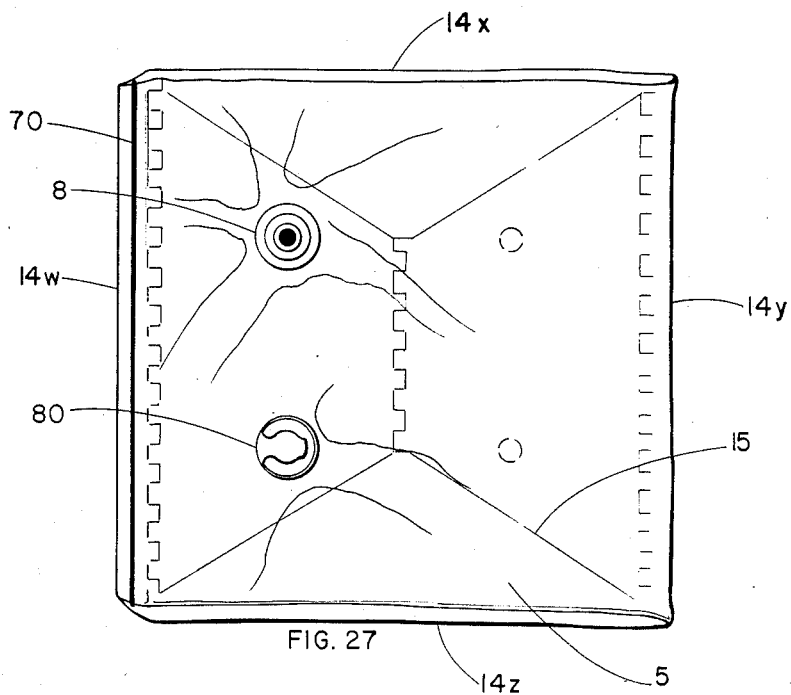
FIG. 27 is a top view of the evacuator of FIG. 26 shown in its fully collapsed and unengaged position.
Figure 28:
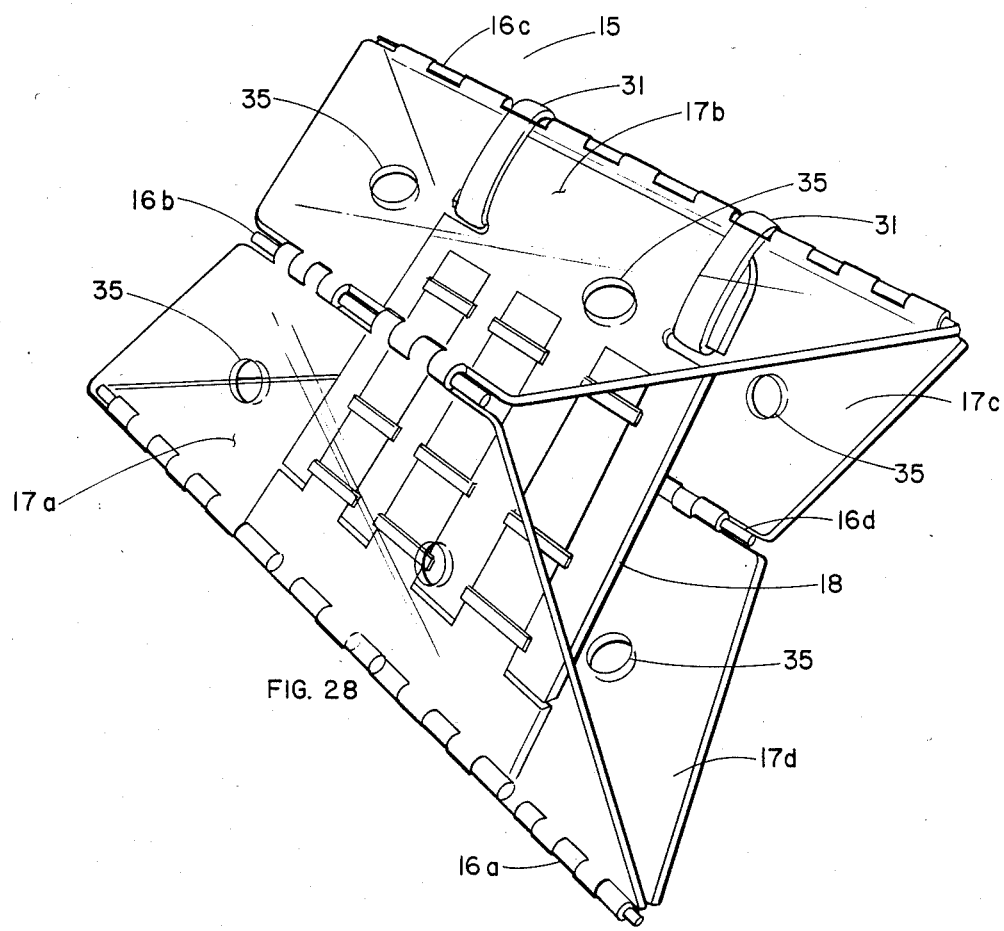
FIG. 28 is a perspective view of a particularly advantageous embodiment of the internal body structure for the evacuator of FIG. 26 illustrating the structure in its fully expanded position.

FIGS. 26–28 illustrate an evacuator 1 according to the present invention in which the side panels 17 are each substantially trapezoidal in shape. The longer base parallel edge of trapezoidal panels 17a and 17d are connected by hinge 16a, while the longer base parallel edge of trapezoidal panel 17b and 17c are connected by hinge 16c. The shorter parallel edge of trapezoidal panels 17a and 17b are connected by hinge 16b, while the shorter parallel edge of trapezoidal panels 17c and 17d are connected by hinge 16d. The center panel 18 is hingedly connected to hinge 16a, and center panel 18 extends diagonally toward the oppositely located hinge 16c as with the previously described embodiment. The center panel 18 may conveniently be approximately the same width as the shorter parallel edge of the trapezoidal panels 17.

A convenient geometry for the pouch 5 which would be suitable for the internal structure 15 having trapezoidally shaped panels 17 is a substantially four-sided rectangular configuration as shown in FIG. 27. The sides are designated as 14w, 14x, 14y and 14z. As with the hexagonal pouch 5, previously described, the rectangularly shaped pouch 5, shown in FIG. 27 may be formed by folding a single sheet of the pouch material over to form a folded of the pouch material over to form a folded edge 14y. The upper and lower layers of the pouch 5 may then be sealed to each other, such as with a heat seal, along edges 14x and 14z, leaving edge 14w open. The internal structure 15 with the trapezoidal panels 17 may then be inserted into the pouch 5 through open edge 14w. After internal structure is inserted, edge 14w may be sealed with a fluid tight seal. FIG. 27 shows edge 14w sealed with a heat seal along line 70 to close edge 14w and provide a fluid tight pouch 5.

When the internal structure 15 is expanded within the pouch 5, as shown in FIG. 26, end portions 130 are drawn slightly inward upon expansion instead of having the triangular portions 13 protruding, as with the embodiment shown in FIG. 1. The combination of the trapezoidal panels 17, as shown in FIGS. 26-28 with the rectangular pouch 5, provides a particularly advantageous combination. With this combination, the pouch 5 expands smoothly and is less likely to get caught in the hinges 16b and 16d (such as when using the type of hinge shown for hinge 16b in FIG. 13). The width and length of the trapezoidal panels may be adjusted depending upon the desired internal volume for the expanded evacuator 1.

The evacuator 1 of the present invention may be tailored to produce various vacuum-volume curves, as desired, within the limits of the device, at the time of assembly, without the addition of components. Since the outward force generated by the device will follow a standard tangent curve with a constant internal force, the vacuum would be low initially and increase as the unit expanded. Additionally, the rate of increase would increase until the device was fully expanded to its square configuration. Conversely, a band or loop made of rubber or other elastomeric material, such as band 31, exhibits a similar stress/strain curve, with a decreasing rate of strain with constant increase in stress. The band will pull harder the more it is stretched. Since the band is extended most, and therefore pulls hardest, when the outward force component of the device is the lowest, by judicious choice of band characteristics and attachment points, various vacuum-volume curves can be produced. These factors can be predetermined to provide a particular evacuator 1 with the desired level of vacuum draw, preferably a moderate to low level of vacuum draw. FIG. 19 shows one means of providing a plurality of attaching points through the use of notches 57 to selectively achieve various vacuum-volume curves. Therefore, the distance that the tensioning means will be stretched when the evacuator 1 is engaged and collapsed can vary depending upon the position to which the tensioning means or force creating means is attached.

The evacuator 1 may be further modified to produce other variations of vacuum-volume curves. For example, a plurality of tensioning means, such as elastomeric bands 31 could be utilized which would be sequentially activated. For example, an embodiment with three elastomeric bands 31 (not shown) could be provided, such that two bands 31 are of equal length with one placed on the front side and one placed on the rear side (similar to the two bands shown in FIG. 9). The third band (not shown) could be positioned centrally between the two outside bands, with the third band having a longer length than the two side bands. When the evacuator 1 is fully collapsed, all three bands are stretched, but as the evacuator expands, the middle longer band becomes loose and is no longer exerting force to expand the evacuator, while the two outside shorter bands are still stretched and exerting a force to cause further expansion of the evacuator to its fully expanded position. This embodiment helps the force or vacuum draw start out higher as initial expansion begins than it would with just the two outside bands. Since the middle band only exerts a force for the initial portion of the expansion and then does not continue to exert a force for the latter portion of the expansion, as the middle band loosens or is no longer stretched, the force does not get as high as it would if the three bands were all pulling for the whole expansion time. This provides a more constant level of vacuum draw than if all the bands were exerting a force for the whole time of expansion. Three or more variations in band length may also be utilized, as desired, to provide such a sequential activation. The varied lengths should be applied in a uniform manner to provide a balance pull.

Another alternate embodiment may include an internal structure 15 which does not collapse fully when compressing the structure 15 to activate it for use. A stop means, such as a protruding member (not shown) on the center panel 18, may be provided such that when compressing the evacuator, the stop means prevents the internal structure 15 from collapsing all the way, thus providing some initial angulation to the evacuator to provide an initial vacuum force upon initial expansion of the evacuator 1.

While this invention has been described in terms of a particularly advantageous embodiment and various modifications, those skilled in the art can appreciate that other modifications can be made without departing from the spirit and scope of this invention.

We claim:
1. A surgical wound evacuator comprising:
   a polygonal hollow enclosure having a plurality of substantially planar, rigid walls interconnected by a plurality of hinges so as to be collapsible and expandable;
   a flexible fluid tight pouch surrounding said enclosure so as to be collapsible and expandable therewith, said pouch having communicating means permitting fluid evacuation from said pouch therethrough during collapse and fluid suction therethrough during expansion; and
   resilient means interconnected between at least two of said hinges, said resilient means permitting collapse of said enclosure and pouch and producing expansion when operably interconnected between said at least two hinges and wherein said resilient means includes a resilient portion and a rigid panel connected to each other to form the resilient means, said panel extending diagonally between two diametrically located opposite hinges.

2. An evacuator as claimed in claim 1 wherein said diagonal panel has a first end and a second end, said first end being hingedly connected to one of said two oppositely located hinges and said second end being connected by the resilient portion to the other opposite hinge of said two oppositely located hinges.

3. An evacuator as claimed in claim 2 wherein said enclosure includes four side walls hingedly interconnected.

4. An evacuator as claimed in claim 3 wherein said side walls are substantially square, flat panels.

5. An evacuator as claimed in claim 3 wherein said side walls are substantially trapezoidal, flat panels each trapezoidal panel having its longest side positioned along one of the oppositely located hinges between which the center panel extends.

6. An evacuator as claimed in claim 2, wherein the first end and second end of the diagonal panel are two separate center portions connectable in a sliding relationship with each other by a connecting portion, such that the two center portions may be either lockingly engaged with each other to functionally form a single panel such that when the evacuator is collapsed by a compressive force, the resilient portion is operatively engaged and therefore is stretched to allow the evacuator to be activated, whereupon release of the compressive force causes the evacuator to expand; or the two separate center portions may be in an unengaged state such that when the evacuator is collapsed, the first end slides towards the hinge to which it is hingedly connected and the second end slides toward the opposite hinge to which it is connected by the resilient portion, hence not causing the resilient portion to be stretched and therefore allowing the evacuator to be collapsed and remain in a non-activated collapsed state.

7. An evacuator as claimed in claim 6 wherein the connecting portion between the first and second ends includes at least one extending finger on one of the center portions positioned in sliding relation between a corresponding finger-receiving opening in the other center portion and wherein said sliding mechanism includes a latching means for operatively engaging the first end to the second end such that the first and second ends may be snapped together to form a single piece diagonal panel which extends from the one of said two oppositely located hinges to the opposite hinge when the enclosure is fully expanded.

8. An evacuator as claimed in claim 7 wherein one of the center portions includes three extending fingers positioned in sliding relation between three corresponding finger-receiving openings in the other center portion.

9. An evacuator as claimed in claim 8 wherein the latching means includes: (1) a latch bar located toward the far end of each finger-receiving opening and extending across the top side of each of said openings, and (2) a correspondingly located protrusion on each of said fingers, each protrusion having a sloped surface which slopes up from the surface of the finger to allow the protrusion to slide under the latch bar, as the two center portions are pushed into engagement with each other, said protrusion having a shoulder which drops down from the peak of the slope back to the finger surface which locks against the latch bar after the protrusion has passed underneath the latch bar thereby engaging the two center portions together.

10. An evacuator as claimed in claim 8 wherein said corresponding finger-receiving openings include a plurality of alignment extensions to keep the intersliding fingers and openings in proper alignment with each other.

11. An evacuator as claimed in claim 2 wherein said second end of the center panel includes an attachment means for engaging the resilient portion from said opposite hinge to the second end of the center panel.

12. An evacuator as claimed in claim 11 wherein said attachment means is a notch along either side of the second end for attachment of said resilient portion to the second end.

13. An evacuator as claimed in claim 11 wherein said attachment means includes a plurality of notches along either side of the second end for selectively attaching the resilient portion to the second end in the desired notch position.

14. An evacuator as claimed in claim 2 wherein each hinge is comprised of an elongated pin member and a series of corresponding interlocking tubular projections extending from each rigid wall such that when the projections extending from one wall are interlocked with the projections from an adjacent wall, a tubular channel is provided through which the pin member is inserted, thereby providing a hinge, and wherein said first end of the diagonal panel also includes interlocking tubular projections which are spaced accordingly to hingedly interlock with the interlocking projections of two of the mating walls.

15. An evacuator as claimed in claim 2 wherein the rigid walls are made from polypropylene and wherein the edges of the walls which meet to form both the hinge for connecting with the first end of the diagonal panel as well as the opposite hinge each include a series of interlocking tubular projections extending therefrom such that when the projections extending from one wall are interlocked with the projections from an adjacent wall, these projections form a tubular channel to form said both hinges, said both hinges each further including an elongated pin member for inserting through each respective tubular channel, thereby providing said both hinges, and wherein the remaining hinges are integrally formed of polypropylene on the edges of the corresponding walls which meet to form the remaining hinges.

16. An evacuator as claimed in claim 1 wherein said pouch contains an opening therein and wherein said enclosure is insertable into the pouch through the opening, said evacuator further including a closure means for sealing off the opening in the pouch after said enclosure has been inserted in the pouch.

17. An evacuator as claimed in claim 16 wherein said pouch is comprised of an upper layer and a lower layer.

18. An evacuator as claimed in claim 17 wherein said pouch is made of vinyl.

19. An evacuator as claimed in claim 17 wherein said pouch has a six-sided configuration with one of the sides extending outward, said extended side including the opening.

20. An evacuator as claimed in claim 16 wherein said closure means includes a heat seal for sealing off the opening after the enclosure has been inserted into the pouch.

21. An evacuator as claimed in claim 16 wherein said pouch includes an extended portion which includes the opening in said pouch, and wherein said closure means includes a platform member for receiving the extended portion of the pouch, said platform including an elongated groove and a corresponding recessed container, said closure means further including a flap member which includes an elongated protruding ridge, such that the extended portion of the pouch is placed over the platform and over the groove opening, and the flap member is subsequently positioned so that the protruding ridge is received in the groove, hence pushing the extended portion of the pouch down in the groove and into the recessed container and sealing off the opening in the pouch.

22. An evacuator as claimed in claim 21 wherein said flap is hingedly connected to the platform member.

23. An evacuator as claimed in claim 21 wherein said ridge is lockingly engaged in the groove once it is received within the groove.

24. An evacuator as claimed in claim 21 wherein said closure means is manufactured from polypropylene.

25. An evacuator as claimed in claim 24 wherein said flap is integrally hinged to the platform member.

26. An evacuator as claimed in claim 21 wherein said closure means further includes a handle means connected thereto for hanging or carrying the evacuator.

27. An evacuator as claimed in claim 1 wherein said resilient portion is at least one elastomeric band member.

28. An evacuator as claimed in claim 26 wherein the handle means is integrally formed with the platform member of the closure means.

29. An evacuator as claimed in claim 1 wherein said resilient portion is at least one spring member.

30. An evacuator as claimed in claim 1 wherein the rigid walls of the enclosure and the diagonal panel are manufactured from a rigid plastic material.

31. An evacuator as claimed in claim 1 wherein said evacuator further includes a handle means for hanging or carrying the evacuator.

32. An evacuator as claimed in claim 1 wherein said communicating means includes at least one valve member.

33. An evacuator as claimed in claim 1 wherein said communicating means includes a first valve member and wherein said pouch further includes a second valve member for attachment to an external suction source, and wherein application of such external suction to the evacuator through said second valve member when the evacuator is in an expanded position, does not cause collapse of the evacuator.

34. An evacuator as claimed in claim 1 where said walls are non-resilient.

35. A surgical wound evacuator comprising:
a polygonal hollow enclosure having a plurality of substantially planar, rigid walls interconnected by a plurality of hinges so as to be collapsible and expandable, wherein said planar walls are planar in both the collapsed and expanded positions;
a flexible fluid tight pouch surrounding said enclosure so as to be collapsible and expandable therewith, said pouch having communicating means permitting fluid evacuation from said pouch therethrough during collapse and fluid suction therethrough during expansion; and
resilient means interconnected between at least two of said hinges, said resilient means permitting collapse of said enclosure and pouch and producing expansion when operably interconnected between said at least two hinges and wherein said resilient means includes a resilient portion and a rigid panel connected to each other to form the resilient means, said panel extending diagonally between two diametrically located opposite hinges.

36. An evacuator comprising:
a hollow enclosure having a plurality of walls interconnected by hinges so as to be collapsible and expandable;
a flexible fluid tight pouch surrounding said enclosure so as to be collapsible and expandable therewith, said pouch having communicating means permitting fluid evacuation from said pouch therethrough during collapse and fluid suction therethrough during expansion; and
a connecting assembly extending between two of said hinges, said assembly including a resilient means permitting collapse of said enclosure and pouch and producing expansion, biasing said two hinges toward each other, when operably interconnected between said two hinges, and said assembly further including a stop means for limiting the movement of said two hinges toward each other.

37. An evacuator as claimed in claim 35 wherein the stop means is comprised of a panel member extending between said two hinges in cooperating relation with said resilient means.

* * * * *